US00RE38670E

(19) United States
(12) Reissued Patent
Asah et al.

(10) Patent Number: US RE38,670 E
(45) Date of Reissued Patent: Dec. 14, 2004

(54) APPARATUS FOR TISSUE TREATMENT

(75) Inventors: Bjarne Asah, Taastrup (DK); Olav Balle-Petersen, Humlebæk (DK)

(73) Assignee: Asah Medico A/S, Hvidovre (DK)

(21) Appl. No.: 09/973,464

(22) Filed: Oct. 11, 2001

Related U.S. Patent Documents

Reissue of:
(64) Patent No.: 6,074,382
Issued: Jun. 13, 2000
Appl. No.: 08/974,429
Filed: Nov. 19, 1997

(30) Foreign Application Priority Data

Aug. 29, 1997 (DK) ..... 0989/97

(51) Int. Cl.[7] ..... A61B 17/36
(52) U.S. Cl. ..... 606/9; 606/10; 606/11; 606/12; 606/18; 607/88
(58) Field of Search ..... 606/3, 8–19; 607/88–91

(56) References Cited

U.S. PATENT DOCUMENTS

| | | | | |
|---|---|---|---|---|
| 3,307,553 A | | 3/1967 | Liebner | |
| 3,821,510 A | | 6/1974 | Muncheryan | |
| 4,140,130 A | | 2/1979 | Storm, III | |
| 4,587,396 A | | 5/1986 | Rubin | |
| 4,849,859 A | * | 7/1989 | Nagasawa | 362/32 |
| 4,854,320 A | | 8/1989 | Dew et al. | |
| 4,913,132 A | * | 4/1990 | Gabriel | 128/9 |
| 4,938,205 A | | 7/1990 | Nudelman | |
| 5,048,904 A | | 9/1991 | Montagu | |
| 5,106,387 A | | 4/1992 | Kittrell et al. | |
| 5,107,516 A | | 4/1992 | Dressel et al. | |
| 5,330,519 A | | 7/1994 | Mason et al. | |
| 5,344,418 A | | 9/1994 | Ghaffari | |
| 5,382,770 A | | 1/1995 | Anderson et al. | |
| 5,405,368 A | | 4/1995 | Eckhouse | |
| 5,456,260 A | | 10/1995 | Kollias et al. | |
| 5,474,549 A | * | 12/1995 | Ortiz et al. | 606/9 |
| 5,531,740 A | * | 7/1996 | Black | 606/9 |
| 5,588,428 A | | 12/1996 | Smith et al. | |
| 5,620,478 A | | 4/1997 | Eckhouse | |
| 5,628,744 A | * | 5/1997 | Coleman et al. | 606/12 |
| 5,630,811 A | | 5/1997 | Miller | |
| 5,653,706 A | * | 8/1997 | Zavislan et al. | 606/9 |
| 5,720,772 A | | 2/1998 | Eckhouse | |
| 5,735,276 A | | 4/1998 | Lemelson | |
| 5,742,392 A | | 4/1998 | Anderson et al. | |
| 5,743,902 A | * | 4/1998 | Trost | 606/18 |
| 5,779,702 A | * | 7/1998 | Fard | 606/53 |
| 5,810,801 A | | 9/1998 | Anderson et al. | |
| 5,814,040 A | * | 9/1998 | Nelson et al. | 606/9 |
| 5,814,041 A | | 9/1998 | Anderson et al. | |
| 5,820,626 A | | 10/1998 | Baumgardner | |
| 5,830,208 A | | 11/1998 | Muller | |
| 5,833,612 A | | 11/1998 | Eckhouse et al. | |
| 5,836,939 A | * | 11/1998 | Negus et al. | 606/11 |

(List continued on next page.)

FOREIGN PATENT DOCUMENTS

DE 3837248 A1 * 5/1990 ..... A61N/5/06

(List continued on next page.)

*Primary Examiner*—Linda C. M. Dvorak
*Assistant Examiner*—Sonya Harris-Ogugua
(74) *Attorney, Agent, or Firm*—Birch, Stewart, Kolasch & Birch, LLP

(57) ABSTRACT

An apparatus for tissue treatment is provided, comprising a light emitter for emission of a first light beam, director for directing the first light beam towards a target area to be treated, detector for detecting at least one tissue parameter at the target area, and first light beam controller for controlling at least one parameter without interruption of the propagating light beam. The tissue parameter may be selected from the group of texture, elasticity, size and shape. The apparatus may be used for ablating a thin epidermal layer of the derma of a patient and also marks on the tissue such as marks from chloasma, liver spots, red spots, tattoos, blood vessels just below the surface, etc. as well as warts, wounds, hair follicles, etc. may be ablated or treated.

34 Claims, 9 Drawing Sheets

U.S. PATENT DOCUMENTS

| | | | | | |
|---|---|---|---|---|---|
| 5,851,181 | A | | 12/1998 | Talmor | |
| 5,853,407 | A | | 12/1998 | Miller | |
| 5,860,968 | A | * | 1/1999 | Wojcik et al. | 606/10 |
| 5,865,828 | A | | 2/1999 | Jeng | |
| 5,868,731 | A | | 2/1999 | Budnik et al. | |
| 5,868,732 | A | | 2/1999 | Waldman et al. | |
| 5,957,915 | A | | 9/1999 | Trost | |
| 5,995,867 | A | | 11/1999 | Zavislan et al. | |
| 6,110,195 | A | | 8/2000 | Xie et al. | |

FOREIGN PATENT DOCUMENTS

| | | | | | |
|---|---|---|---|---|---|
| EP | 0763371 | A2 | * | 3/1997 | A61N/5/06 |
| EP | 0783904 | A2 | * | 7/1997 | A61N/5/06 |
| EP | 0788765 | A1 | * | 8/1997 | A61B/5/103 |
| EP | 0827716 | A2 | * | 3/1998 | A61B/17/36 |
| EP | 0880941 | A1 | | 12/1998 | |
| EP | 0898983 | A1 | | 3/1999 | |
| EP | 0933096 | A2 | | 8/1999 | |
| WO | WO 86/06527 | | | 11/1986 | |
| WO | WO 98/51235 | | | 11/1988 | |
| WO | WO 93/08877 | | | 5/1993 | |
| WO | WO 94/00194 | | * | 1/1994 | A61N/5/06 |
| WO | WO 95/03089 | | | 2/1995 | |
| WO | WO 96/25979 | | * | 8/1996 | A61N/5/06 |
| WO | WO 98/24514 | | * | 6/1998 | A61N/5/06 |
| WO | WO 98/25528 | | * | 6/1998 | A61B/17/36 |
| WO | WO 98/33558 | | | 8/1998 | |
| WO | WO 98/49963 | | | 11/1998 | |
| WO | WO 98/55180 | | | 12/1998 | |
| WO | WO 98/57588 | | | 12/1998 | |
| WO | WO 99/17668 | | | 4/1999 | |
| WO | WO 93/16631 | | | 9/1999 | |
| WO | WO 99/46005 | | | 9/1999 | |

* cited by examiner

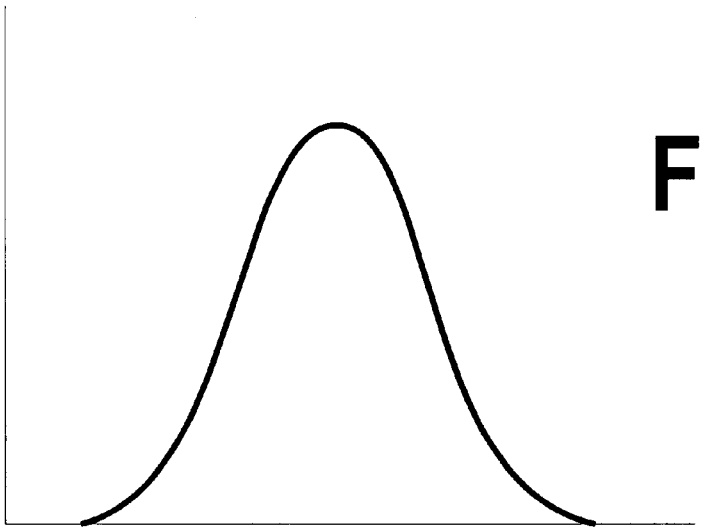
Fig. 9a
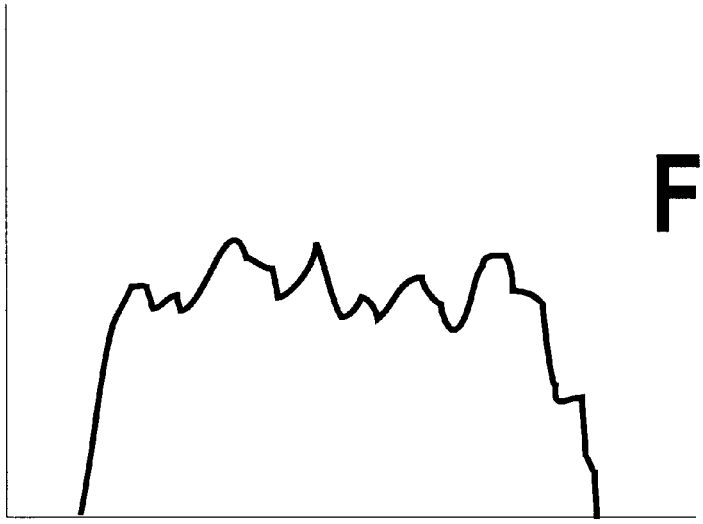
Fig. 9b
Fig. 9

APPARATUS FOR TISSUE TREATMENT

Matter enclosed in heavy brackets [ ] appears in the original patent but forms no part of this reissue specification; matter printed in italics indicates the additions made by reissue.

FIELD OF THE INVENTION

The present invention relates to an apparatus with a handpiece for tissue treatment, such as cosmetic tissue resurfacing.

BACKGROUND OF THE INVENTION

It is known to utilise laser light for tissue treatment, such as cosmetic tissue resurfacing, removal of hair, photocoagulation of veins, etc.

During cosmetic tissue resurfacing, a laser ablates a thin epidermal layer of illuminated derma of a patient. During healing, a new epidermal layer is formed on the ablated surface having the look of the derma of a young person, i.e. the new epidermal layer is formed without previously existing scars, wrinkles, etc.

Lasers that operate at a wavelength that is absorbed in water are used for cosmetic tissue resurfacing. When the laser power density ($W/mm^2$) at illuminated cells is sufficient, cellular water is superheated causing small explosions that disrupt heated cells.

During removal of an epidermal layer, it is essential not to damage underlying or surrounding tissue. Residual heat may cause non-ablated cells to char and become necrotic, whereby new scars may be formed and thus, it is desirable to apply laser power for a short time, to minimize transmission of conducted heat to underlying and surrounding tissue.

It is therefore desired to accurately control the amount of light energy transferred to derma to be ablated. The amount of energy must be sufficient for the dermal cells to vaporize and, simultaneously, the amount of residual energy heating non-ablated cells must be so low that non-ablated cells will not be damaged.

Apparatuses for cosmetic tissue resurfacing are known, comprising a $CO_2$ laser emitting a laser beam and a laser articulating arm with mirrors for reflection of the laser beam, so that the laser beam is transmitted inside the articulating arm. Further, the arm has a number of joints, so that the arm can be moved around by an operator. A handpiece to be held by the operator is connected to the arm. The laser beam is moved or scanned across a target surface by movable mirrors connected to motors and mounted in the arm. The scan pattern of the laser beam is an archimedes spiral. The laser spot formed by the laser beam on the target surface moves along the spiral at a constant angular speed.

It is a disadvantage of the known apparatus that the energy density delivered to the target surface is non-uniform across the scanned surface area of the spiral, as more energy is delivered at the centre of the spiral than at the circumferential of the spiral.

It is another disadvantage of the known apparatus that the circular outline of the scan pattern leads to non-uniform scanning of an area that is larger than the area of the scan spiral as either 1) areas that have not been scanned will remain on the surface, when abutting spirals or 2) ablated areas will be scanned more than once, due to overlap of spirals.

It is yet another disadvantage of the known apparatus that evaporated derma is exhausted through the internal of the laser articulation arm, whereby optics and other members in the arm get dirty.

It is still another disadvantage of the known apparatus that it is very laborious to disassemble members, that may have been in contact with a patient, from the handpiece, e.g., for autoclaving.

It is still another disadvantage of the known apparatus that movement of the handpiece is restrained by the laser articulation arm, as the construction of tubes interconnected by joints is not fully flexible.

In addition, the apparatus typically has a large mass and a large inertia (typically also due to counter-balancing masses) which makes the operation and movement of the arm elaborate and heavy.

Under the name Uni-laser 450P, Asah Medico A/S, Denmark, markets an apparatus for cosmetic tissue resurfacing, comprising a $CO_2$ laser and an optical fiber coupled to the laser at one end and to a handpiece at the other end. The laser beam is manually scanned across the treatment surface by corresponding movement of the handpiece whereby the quality of the treatment is determined and limited by the skill of the operator.

Apart from being able to accurately control the amount of light energy transmitted towards tissue to be treated, it is also desirable to be able to automatically control whether or not light is transmitted towards tissue. If, for example, a laser is pointed at healthy tissue, it is desirable that it is detected that the tissue is healthy and that transmission of a laser beam be inhibited whereby damage to healthy tissue is prevented.

It is a disadvantage of known apparatuses that the exact circumference of the surface tissue area to be treated is defined manually by the operator. Manual control easily results in accidental damage to healthy tissue due to involuntary movements of the hand.

In U.S. Pat. No. 5,531,740, an apparatus is disclosed for automatically delivering a laser beam to an intricated colored region of a treatment area, e.g. for laser photocoagulation treatment of malformed veins. Typically, venular malformation forms an extremely intricate pattern and consequently, the task of precisely delivering the laser beam exclusively to the malformed veins becomes quite formidable. During scanning over the treatment region, the color of tissue to be treated is detected and the laser automatically treats only areas having a specified color.

It is a disadvantage of the apparatus that it is bulky and cannot easily be moved into treatment positions in relation to various surfaces of a human body. Rather, a tissue surface to be treated has to be brought into a specific position in relation to the apparatus before treatment can take place.

It is still another disadvantage of the known apparatuses that the distance between the surface to be treated and the output laser beam optics is unknown so that the degree of focusing of the laser beam on the surface to be treated is dependent on the operator.

It is yet another disadvantage of known apparatuses that no feed-back on the quality of the treatment currently in progress is provided.

SUMMARY OF THE INVENTION

It is an object of the present invention to provide an apparatus for tissue treatment having a handpiece that can be moved around, i.e. traversed and rotated, freely by an operator, i.e. without exerting forces acting against the movement.

It is another object of the present invention to provide an apparatus for tissue treatment in which tissue type of tissue at the area to be illuminated by the treating light beam is detected and in which parameters of the laser beam is adjusted according to detected tissue type.

It is a further object of the present invention to provide an apparatus for tissue treatment that includes means for detecting the distance between the surface of tissue to be treated and the output optics focusing treating light onto the surface so that optimum focusing conditions may automatically be obtained during treatment.

It is still another object of the present invention to provide an apparatus for tissue treatment that includes a temperature measuring device for measurement of tissue surface temperature.

It is yet still another object of the present invention to provide an apparatus for tissue treatment that is adapted to automatically and accurately treat tissue to a desired depth with causing only a minimum of damage to surrounding tissue that are not treated.

It is a further object of the present invention to provide an apparatus for cosmetic tissue resurfacing that is adapted to ablate dermal cells uniformly and from a large area of a patient.

According to the invention, the above-mentioned and other objects are fulfilled by an apparatus for tissue treatment, comprising a light emitter for emission of a light beam and an optical fiber for transmission of the light beam. The fiber has a beam-inlet end that is aligned with the emitted light beam so that the light beam is coupled into the optical fiber and a beam-outlet end for emission of the transmitted light beam. Further, the apparatus comprises a handpiece coupled to the optical fiber at the beam-outlet end and comprising an output for emission of the first light beam towards a target area of tissue to be treated, detector means for detecting the type of tissue at the target area, and first light beam control means for controlling parameters of the first light beam emitted towards the target area in response to the detected type of tissue whereby various types of tissue can automatically be treated differently.

Cellular water absorbs light energy and transfers the light energy into heat. Applying light energy to the cells is therefore an efficient way of destroying, e.g. ablating, tissue. That, it is preferred to use light sources, such as lasers, generating light at wavelengths with a high absorption in water, preferably wavelengths larger than 190 nm, such as wavelengths in the range from 190 nm to 1900 nm, preferably from 700 nm to 900 nm, and even more preferred approximately 810 nm, or, preferably wavelengths larger than 1900 nm, such as wavelengths in the range from 1900 nm to 3000 nm, preferably from 1900 nm to 2100 nm, and even more preferred approximately 1940 nm, or, from 2800 nm to 3000 nm, and even more preferred approximately 2930 nm, or wavelengths equal to or greater than 4500 mm, such as wavelengths in the range from 4500 nm to 11000 nm, preferably from 4500 nm to 5500 nm, alternatively from 10000 nm to 11000 nm, such as around 10600 nm.

The apparatus according to the invention may be used for ablating a thin epidermal layer of the derma of a patient, removing marks on the tissue, such as marks from chloasma, liver spots, red spots, tattoos, blood wessels just below the surface, etc, as well as warts, wounds, hair follicles, etc, and hereafter the terms tissue and resurfacing will include these marks and treatments thereof.

It is preferred, that the light source utilized in the present invention is a laser, but other light sources, such as light emitting diodes and halogen bulbs, may be utilized.

The laser may be any laser capable of emitting light with sufficient power for illuminated cells to vaporize, such as $CO_2$ lasers, YAG lasers, such as Erbium YAG lasers, Holmium YAG lasers, etc., semi conductor lasers, pulsed lasers, gas lasers, solid state lasers, Hg lasers, excimer lasers, etc.

Typically, a power density greater than about 50 W/mm$^2$, such as a power density in the range from about 50 W/mm$^2$ to about 180 W/mm$^2$, is adequate for vaporizing cells with a minimum of damage to the surrounding tissue.

However, when removing hairs, the wavelength of the light is preferred to be approx. 800 nm. At this wavelength the absorbtion of the light in the hair follicles is lower than at higher wavelengths, and the power density must therefore be higher than 180 W/mm$^2$, preferable higher than 300 W/mm$^2$. Generally, the power density is adapted to the wavelength and the tissue to be treated.

The optical fiber may be any fiber, such as a polycrystalline silver halide fiber, etc, that is suitable for transmission of light emitted from the light emitter and that is made of a material that allows repeated bending of the fiber, so that an operator can freely manipulate the handpiece in order to direct the light beam toward various areas of a patient.

A handpiece is a single unit for conveniently holding in one hand by an operator of the handpiece.

It is preferred to shape the handpiece ergonomically so that a comfortable hand grip is provided for the operator of the apparatus. For example, it is preferred to direct the light beam towards a target area at a substantially right angle to the area. The ergonomic form of the handpiece allows the operator to point the light beam at a substantially right angle to the target surface without having to bend the wrist in an uncomfortable way.

As already mentioned, it is desirable to automatically control whether or not tissue towards which the hand piece is directed (the hand piece is said to be directed towards a specific area if that area is illuminated when the light beam emitted by the handpiece is turned on) is treated and to what extent it may be treated. For example, if the handpiece is directed towards healthy tissue, turn on of the light beam should be inhibited.

Tissue may be classified into specific tissue types according to predetermined values of various parameters, such as color, temperature, texture, elasticity, size, shape, etc.

For example various marks may be detected by their color. Thus, the detector means may comprise light detectors for detection of intensity of light emitted from tissue at the target area, the target area being the area the handpiece is currently directed at.

The light detector is preferably a semiconductor light detector, such as a photodiode, etc.

Further, the handpiece may comprise two light sources emitting light of different wavelengths, preferably two light emitting diodes, one for emission of light in the wavelength range where the light is considered red and the other for emission of light in the wavelength range where the light is considered green. The light sources may alternatively emit light in the ultra violet or infrared wavelength range. Light from the light sources is transmitted towards the target area and is reflected by tissue at the target area. The reflected light is detected by the detector means and the intensity of reflected light in the two wavelength ranges in question characterizes the type of tissue that is illuminated.

The first light beam control means comprises outputs for controlling various parameters of light emitted by the light emitter, such as wavelength, output power, duty cycle, etc. Based on tissue type parameter values as measured by the detector means, the first light beam control means adjusts parameters of the emitted light correspondingly. For example, when two light sources are utilized for detection of tissue type as previously described, predetermined reflected light intensity value ranges for the two wavelength ranges may be stored in a memory of the first light beam control means. During treatment, measured values of reflected light intensity are compared with the stored predetermined ranges and when measured values are within the stored ranges treatment is enabled and otherwise it is disabled.

Further, the wavelength and/or the power of treating light emitted by the light emitter may be adjusted according to the measured values. For example, a plurality of predetermined ranges of reflected light intensity may be stored in the memory and during treatment the measured values may be compared to the stored ranges and the value of the wavelength and/or the power of treating light may be set according to relations between measured values and stored ranges. Alternatively, the first light beam control means may calculate and control the wavelength and/or the power of treating light as a predetermined function of measured values of reflected light.

The output power of the first light beam may be adjusted by adjustment of the continuous output power of the light emitter, by adjustment of the duty cycle of the light emitter, etc.

The handpiece may comprise an infrared detector, such as an infrared photodetector, for detection of intensity of infrared light emitted from tissue at the target surface, e.g. for determination of the temperature of the tissue. Like color, temperature may be utilized for characterization of tissue types. Further, tissue temperature may be utilized for monitoring of treatment progress and quality. The temperature of treated tissue increases during treatment and measurement of tissue temperature may be utilized for verification of the effect of the treatment. For example, when a specific tissue temperature is reached within a specific area, treatment of that tissue may be terminated, e.g. further treatment may be inhibited, as sufficient treatment has already been accomplished. Further, if a certain temperature has not been reached during treatment, output power of the light emitter may be increased to increase efficiency of the treatment.

To obtain an optimum result of treatment, it is important to keep the light beam focused at the target area during treatment.

The handpiece may comprise means for automatically controlling the distance from the handpiece of the focus point in such a way that the light beam is automatically focused at the target area during treatment.

Thus, the detector means may comprise a detector array and array optics for forming an image of the target area on the array. Further, the detector means may comprise image processing means for processing the output signals from the detector array. Preferably, the imaging means is adapted to calculate the size of a spot of light illuminated by the first light beam, or another light source of the apparatus, and imaged onto the detector array.

The handpiece may further comprise output optics for focusing the first light beam onto the surface of tissue to be treated and movably positioned at the output of the handpiece for adjustment of the distance between the handpiece and the focus point, and focus control means for adjusting the position of the output optics in repsonse to the value of the calculated spot size.

According to another embodiment of the invention, two crossing visible light beams are emitted from the handpiece, the cross point of the beams indicating the focus point of the first beam. The imaging means are adapted to detect the number of spots imaged onto the detector array, and the focus control means are adapted to adjust the position of the output optics in response to the number of spots and, preferably, the distance between them (if more than one).

The handpiece may comprise deflection means that includes any optical component or components suitable for deflecting light of the wavelength in question, such as mirrors, prisms, grids, diffractive optical elements, such as holograms, etc, etc.

The deflecting means are preferably movably mounted for displacement of the deflecting means as a function of time, so that the light beam emitted from the handpiece can be scanned across a surface along a desired curve, while the handpiece is kept in a fixed position. Preferably, the deflecting means are rotatably mounted, and the actual deflection of the light beam is determined by the current angular position of the deflecting means. It is preferred that the surface is scanned along a substantially straight line.

Various actuators may be utilized to control positions of the deflecting and focusing means, such as piezo electric crystals, the displacement of which is controlled by applying a specific electric voltage to their electrodes, electro motors generating linear or rotational displacements, galvanometers, magnetically activated or controlled actuators, pneumatic actuators, hydraulic actuators, etc.

The positions of the deflecting means may be controlled by controlling means adapted to control the deflection means to deflect the light beam to traverse a target surface along a desired curve.

According to a preferred embodiment of the invention, a handpiece is provided, having two mirrors that are rotatably mounted in the path of the light beam in the handpiece. The rotational axis of the mirrors may be substantially perpendicular to each other in order to obtain two dimensional deflection of the light beam.

Alternatively, the movable deflecting means may comprise one mirror that is rotatable around two axes that may be substantially perpendicular to each other.

The mirrors may be connected to electro motors for angular positioning of the mirrors, e.g. each mirror may be directly connected to a corresponding shaft of a motor, whereby each motor is used for angular positioning of the corresponding mirror.

In order to minimize the size of the handpiece, it is preferred to mount the motors with their respective shafts in a common plane. For example, one motor may be a linear motor, such as a linear step motor, generating linear displacements. The shaft of this motor may be connected to the mirror at a first edge of the mirror, while a second and opposite edge of the mirror is rotatably connected to the handpiece. By pushing or pulling the first edge by the linear motor, the mirror is rotated about its rotational axis. The other motor, preferably a galvanometer, may be connected to the other mirror in the conventional way described above, whereby the two mirrors may be rotated around substantially perpendicular axes.

When a target area is scanned line by line, it is preferred that movement of one mirror generates the line scan, while movement of the other mirror moves the light beam to the next line. In the example above, the galvanometer preferably generates the line scan as the galvanometer can move the mirror at a high speed, and the linear motor preferably generates the displacement of the light beam to the next line to be scanned.

As mentioned earlier, it is preferred to control the amount of energy delivered to cells to be ablated, as the amount of energy must be sufficient for the dermal cells to vaporize and, simultaneously, the amount of residual energy heating non-ablated cells must be so low that non-ablated cells will not be seriously damaged. Thus, when an area of tissue is scanned, e.g. line by line, it is preferred that neighbouring lines substantially abut each other. Clinical investigations have shown that, typically, an overlap of 0.1 to 0.2 mm is acceptable, and a distance between scanned areas of up to 0.1–0.2 mm is acceptable.

In order to control positioning of curves on the target area this accurately, it is preferred to position the movable deflection means extremely accurately in the handpiece. In the preferred embodiment of the invention, this is accomplished by utilisation of printed circuit technology providing high accuracies of hole positioning of 0.05 mm. The mirrors are rotated around shafts that are mounted in printed circuit boards providing the required positioning accuracy. Further, the motors rotating the mirrors are also mounted on the printed circuit boards providing electrical connections to the motors and the mechanical support and positioning needed.

When scanning a scan area line by line, it is preferred to scan each line in the same direction ensuring uniform heating of cells across the scan area. Further, it is preferred to turn off the light beam, e.g. by switching off the light emitter, by inserting a light obstructing member in the light path of the beam, etc, while the light beam is moved from the end of a line having been scanned to the start of the next line to be scanned, to avoid over illuminating areas of the two lines to be scanned.

Instead of turning the light emitter off, the light beam may be moved at a speed significantly larger than the scan speed, during movement from the end of a line to the start of the next line.

Typically, the intensity within the beam of a light beam as generated by the light emitter varies as a normal function of the distance from the centre of the beam. The optical fiber may be designed or selected to be dispersive in such a way that the intensity function of the light beam emitted from the fiber as a function of the distance to the centre of the beam is substantially rectangular, i.e. the intensity of the beam leaving the fiber decays more slowly towards the edge of the beam than the intensity of a beam as generated by the light emitter whereby heat is more uniformly generated in cells across a scanned line of tissue.

By adequate control of the starting position of a line to be scanned and the stop position of scanning along the line, it is seen that scan areas of any shape may be generated. The shape of the scan area may for example be polygonal, such as rectangular, quadratic, triangular, etc., or circular, elliptic, etc.

The detector means may be utilized for detection of various tissue parameters during scanning of the first light beam across a tissue area so that treatment and tissue parameter determination are performed substantially simultaneously including adjustment of light beam parameters according to detected tissue parameter values.

However, it is presently preferred that the light beam control means further comprises switching means for preventing emission of the first light beam and being controlling by the first light beam control means so that emission of the first light beam is prevented during a first scan of the light beam from a predetermined first position to a predetermined second position along a predetermined path. The apparatus may further comprise tissue type storage means for storage of coherent data sets of signal values provided by the detector means at predetermined positions along the predetermined path of the light beam and the corresponding positions of the deflection means thereby mapping tissue parameters as a function of relative position within the target area of the tissue in the storage.

The first light beam control means may further be adapted to control parameters of the first light beam during a second movement of the light beam along the above-mentioned predetermined path in accordance with the coherent data sets stored.

For example, without automatic control of tissue treatment, removal of hair is a difficult task to perform as a large number of small spots having diameters of approximately 1 mm have to be pinpointed by the operator performing the treatment. According to the present invention, the surface tissue area with hair to be removed is scanned by the handpiece. Hereby the hair follicles are detected by color determinations as described above and their positions along the scanned path of the light beam are stored in the tissue type storage means. During a second and repeated scan of the tissue area, the treating light beam is turned on and off according to the content of the tissue type storage means so that solely the hair follicles detected during the first scan are treated preventing the surrounding tissue from being damaged.

Parameter values, such as color, temperature, etc, stored in the tissue type storage may be displayed on a display unit, such as a CRT, LCD, etc, e.g. as graphical three dimensional plots showing surface profiles of the actual parameters of scanned areas. Further, the parameter values may be processed, e.g. providing averages, weighted averages, correlation, cross-correlation, etc, and the value may be displayed, e.g. on the display unit or, on a separate display on the handpiece.

The output power of the first and treating light beam may be adjusted by adjusting the duty cycle of the beam, i.e. by pulse width modulating the light emitter. Thereby, a scanned line is broken into a plurality of line segments. A fade-in scan area may be created by starting the line with short pulses of light between longer periods of no light. As the line is traversed, the duration of light pulses is gradually increased and the periods with no light is gradually decreased. Finally, at the end of the fade-in area the light is not pulsed, and the scan line may be completed with maximum light intensity.

Similar, a fade-out scan area may be created by starting a scan line with maximum light intensity, and at the start of the fade-out area, the light emitter is pulse width modulated to transmit shorter and shorter pulses of light between longer and longer periods of no light. Finally, at the end of the fade-out area, the light is not pulsed, and the scan line is completed with no light intensity.

Fade-in or fade-out scan patterns may also be created by gradually increasing or decreasing, respectively, the output power of the light emitter, or by decreasing or increasing, respectively, the scan speed of the light beam, i.e. the speed at which the spot illuminated by the first light beam moves on a surface to be treated.

Alternatively, any combination of these methods may be used.

Various shapes, such as polygonal, such as rectangular, quadratic, triangular, etc, circular, elliptic, etc, of the area including fading area to be scanned by the first light beam may be selected by the user. Within the selected shape, treatment of tissue may be automatically controlled as described above, e.g. a rectangular shape of an area to be treated may be selected, however, if the handpiece is directed at healthy tissue the area will be scanned to determine tissue type and no treatment will be performed.

A scan line with fade-in and/or fade-out effects creates a smooth transition from a non-treated area of the tissue to a treated area of the tissue. This is advantageous when using the apparatus of the present invention for treatment of small marks on the tissue such as marks from chloasma, liver spots, red spots, tattos, blood wessels etc.

The first light beam control means may be adapted to control the intensity of the light beam and/or the velocity of the scanning light beam along a desired curve as a function of the position of the light beam inside the area of the target tissue area.

Within an area of tissue all of which is of a type to be ablated, the first light beam control means may be adapted to provide a substantially constant intensity of the light beam and a substantially constant scan velocity of the first light beam.

If desired, the fade-in and fade-out effect may be provided either by scanning the light beam with a velocity larger than the substantially constant scan velocity within the treatment area of tissue or, by decreasing the output power of the first light beam.

The first light beam control means may be adapted to control the power-per-area of the light beam when scanned along a desired curve on a target tissue area to be treated. For example, when ablating tissue it is presently preferred to maintain the power-per-area of the first light beam inside a first part of the target tissue area at a substantially constant level.

In order to create the fade-in or fade-out effect, the power-per-area of the light beam when outside a first part of the target tissue area may depend on the distance to the first part of the target tissue area, and it is preferred that the power-per-area of the light beam increases with decreasing distance to the first part of the target tissue area.

In the case where the first light beam is invisible, e.g. utilizing an infra red emitter, an ultra violet emitter, etc, a light source generating visible light may be provided for generating a visible light beam that is used to assist the operator by indicating areas towards which the invisible and treating light is directed during scanning. For example, the input connector of the handpiece may be further adapted to connect a second beam-outlet end of a second optical fiber for transmission of a visible light beam to the handpiece. The second optical fiber is preferably properly aligned in the connector in relation to the desired path of the visible light. The handpiece may further comprise second movable deflecting means for variable deflection of the visible light beam in such a way that the treating light beam and the visible light beams emitted from the output of the handpiece illuminate substantially the same area of a target surface.

Further, two crossing visible light beams may be emitted from the handpiece, the cross point of the beams indicating the focus point of the first beam.

Preferably, common moving deflecting means are utilised for deflection of all light beams emitted from the handpiece. Zinc selenite lenses may be utilized, as they are transparent for visible light as well as for infra-red light.

In order to further assist the operator of the apparatus, the visible light beam may, e.g. between scans of the treating light beam, be scanned around at least a part of the circumference of the scan area thereby indicating the size, shape and position of the scan area to be scanned.

When a polygonal shape of the scan area has been selected, the visible light beam may, e.g. between scans of the ablating light beam, be scanned along one edge of the polygon.

In order to further assist the operator of the apparatus, the temperature of the target tissue area may be measured immediately after treatment. The surface temperature is measured by measuring the infrared irradiation from the surface with the detector means of the handpiece. This temperature provide an objective measure of the quality of the treatment. A high temperature in the surface skin indicates that the energy has been absorbed in the surface tissue, whereas a low surface temperature indicates that the energy has been absorbed in the depths of the tissue. It is also possible to provide an interface to a PC (or any other calculating unit) for further calculations on the temperature data.

In order to assist the operator of the apparatus in keeping a constant distance from the output of the handpiece to the surface of the tissue to be ablated, the handpiece may comprise a distance member connected to the handpiece at the output with fastening means.

As the distance member will touch the patient, it is desirable to insert a new, disinfected member before treatment of a new patient and thus, it is preferred that the fastening means comprises a magnet so that a used distance member can easily be disconnected from the handpiece, e.g. for autoclaving, and so that a new member can easily be connected to the handpiece.

In order to increase the ease of use of the handpiece, it may be provided with interfacing means for selection of parameters of the cosmetic resurfacing apparatus. The interfacing means may comprise push buttons, selectors, rotary switches, etc. The interfacing means may also comprise a display for showing the mean temperature of the surface immediately after the treatment.

The parameters selectable from the handpiece may comprise the scan velocity, the ablating and the visible light beam intensities, the size and shape of the scan area, and fade-out effects.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

In the following, a preferred embodiment of a tissue treatment apparatus comprising detector means will be described with reference to the drawings, wherein

FIG. 9 shows a cross section of a standard laser beam and an example of a cross section of a laser beam more suitable for use in the handpiece of the present invention.

DETAILED DESCRIPTION OF THE DRAWINGS

Figure 1:
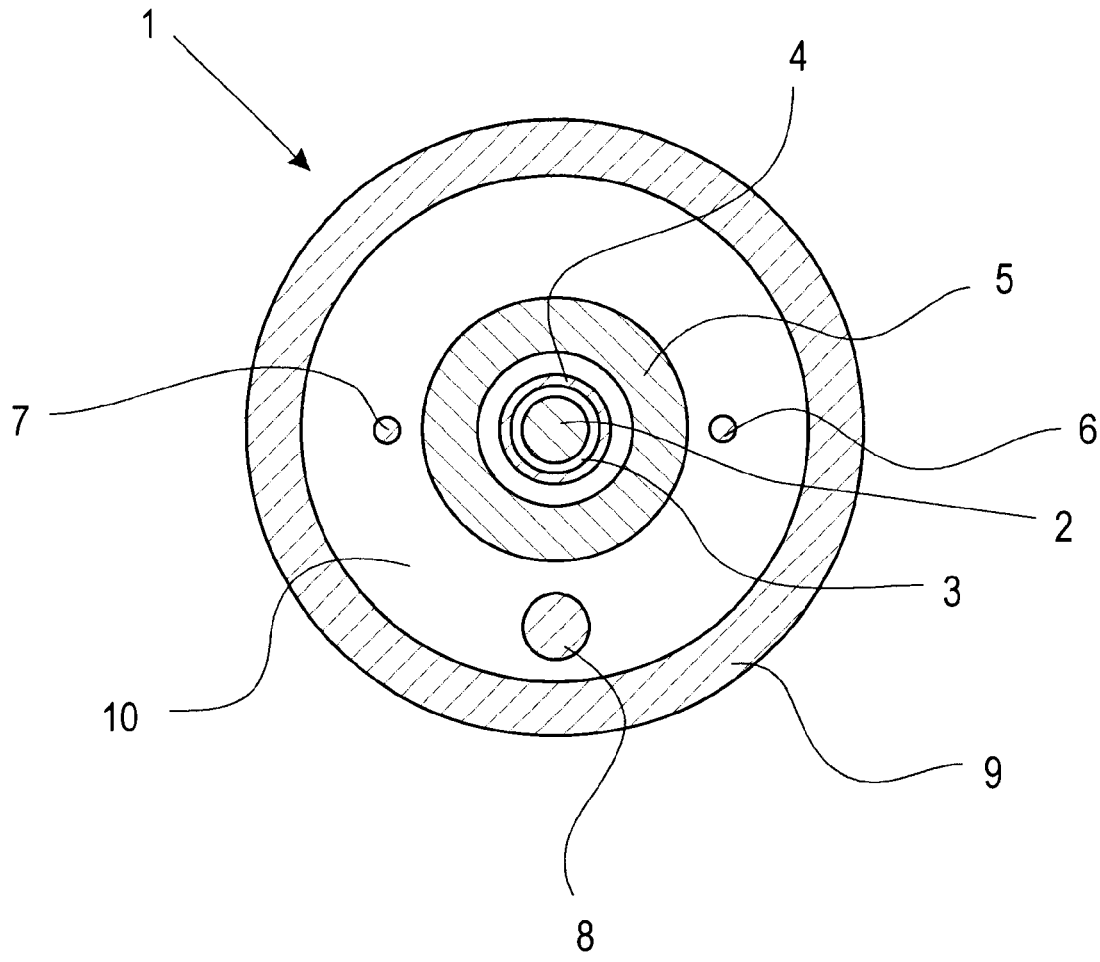
FIG. 1 shows a cross section of a cable for transmission of light from a laser source to the handpiece according to the invention.

FIG. 1 shows a cross section of a cable 1 for transmission of light from a laser source to the handpiece of an apparatus for tissue treatment. An optical fiber 2 is positioned at the centre of the cable 1. The optical fiber 2 is made of silver chloride and silver bromide (silver halide), which is especially designed for light at a wavelength of app. 10.6 $\mu$m. The optical fiber 2 is covered by a cladding 3, also made of silver bromide and silver chloride but mixed in another ratio, which prevents the light travelling in the fiber 2 to escape from the fiber 2. The diameter of the fiber 2 is app. 500 $\mu$m, while the cladding 3 is app. 50 $\mu$m thick. The fiber 2 and the cladding 3 are protected against influence from the environment by a teflon tube 4. The fiber 2 and the cladding 3 are also protected against mechanical stress by a plastic tube 5 also protecting the teflon tube 4. The fiber 2, the cladding 3, the teflon tube 4 and the plastic tube 5 can be considered as an optical fiber unit 10. Included in the cable 1 are two glass fibers 6, 7 and a wire 8. The two glass fibers 6, 7 are specially designed optical fibres designed with a small NA (numerical aperture) designed for visible light at a wavelength of app. 650 nm. The wire 8 is provided for protecting the cable 1 against tensions and overloads. The optical fiber unit 10, the two glass fibers 6, 7, and the wire 8 are surrounded by a spiral tube 9 made of stainless steel. The optical fiber unit 10, the two glass fibers 6, 7, and the wire 8 are not fixed in position relative to each other inside the spiral tube 9, but can move in relative to each other inside the spiral tube 9, but can move in relation to each other. This makes the cable 1 very flexible when it is moved, and it provides at the same time a good protection of the fragile fibers 2, 6, 7. Inside the spiral tube 9 and along the optical fiber unit 10, the two glass fibers 6, 7, and the wire 8, compressed air is blown. The air is blown out in front of the optics, blowing away any ablated material that otherwise could deposit on the optics.

The light beam from a $CO_2$ laser is coupled into the optical fiber 2 at one end of the fiber 2 positioned at one end of the cable 1. At the same end of the cable 1, light beams from two diode lasers are coupled into the glass fibers 6, 7, respectively. The light beams are transmitted in the respective fibers from the inlet end to the outlet end, which is connected to a handpiece.

Figure 2:
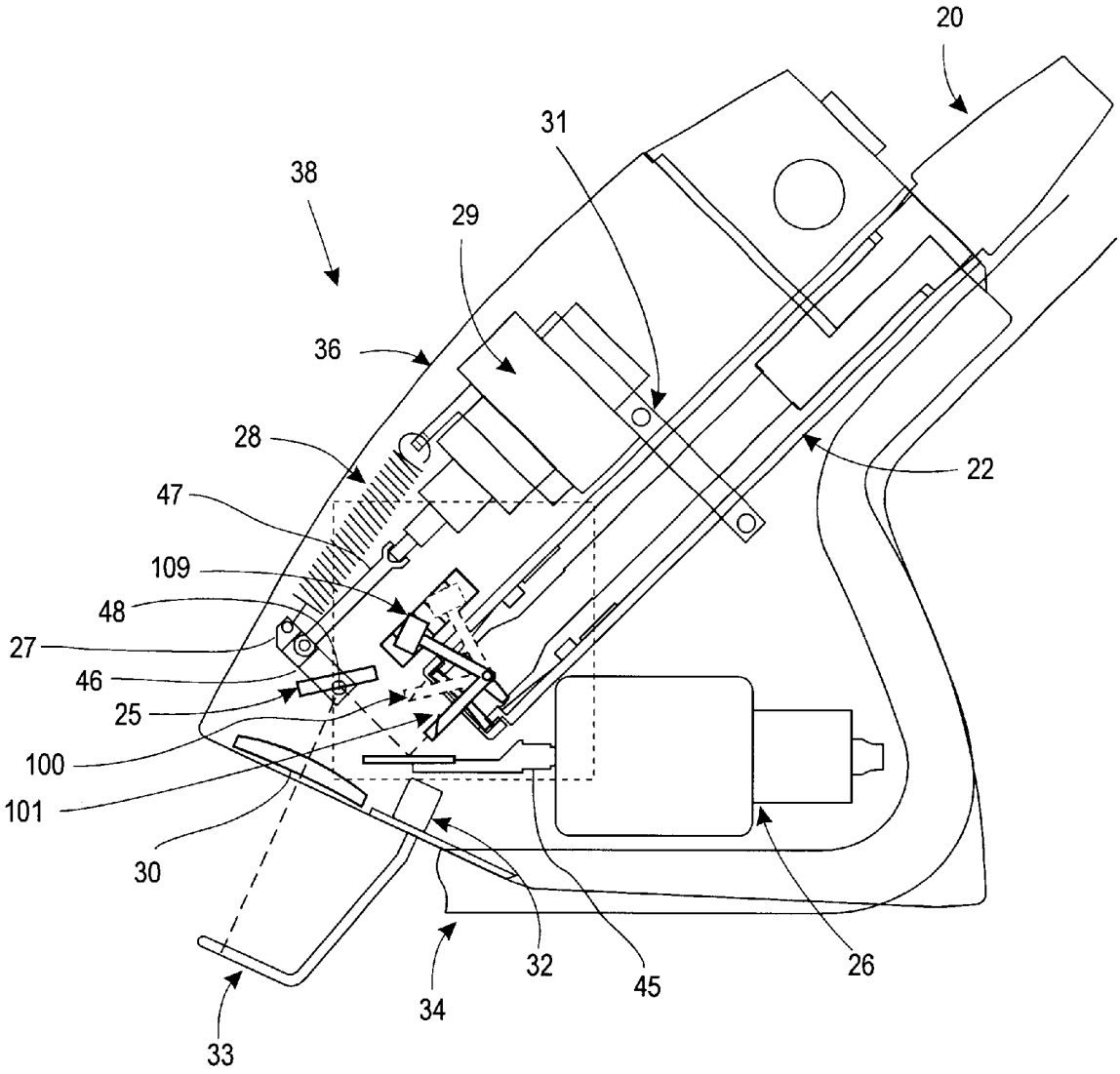
FIG. 2 shows a cross section of a handpiece according to the present invention.

FIG. 2 shows a handpiece 38 of an apparatus for tissue treatment according to the present invention. The cable 1 (not shown in FIG. 2) is connected to the handpiece 38 at a fiber inlet part 20, and guided through a tube 22 which is held in place in the handpiece 38 by the holding and heat distributing means 31. The fiber inlet part 20 also serves as a cable protecting sleeve. The light beams transmitted in the optical fiber 2 and the two glass fibers 6, 7 are radiated from the outlet ends of the fibers 2, 6, 7 through a lens system 39 (see FIG. 3) to an object, e.g. a human tissue surface. The outlet ends of the fibers 2, 6, 7 are positioned at a distance appropriate for the focusing lens 21 to focus the light from the fibers 2, 6, 7 on the object.

Figure 3:
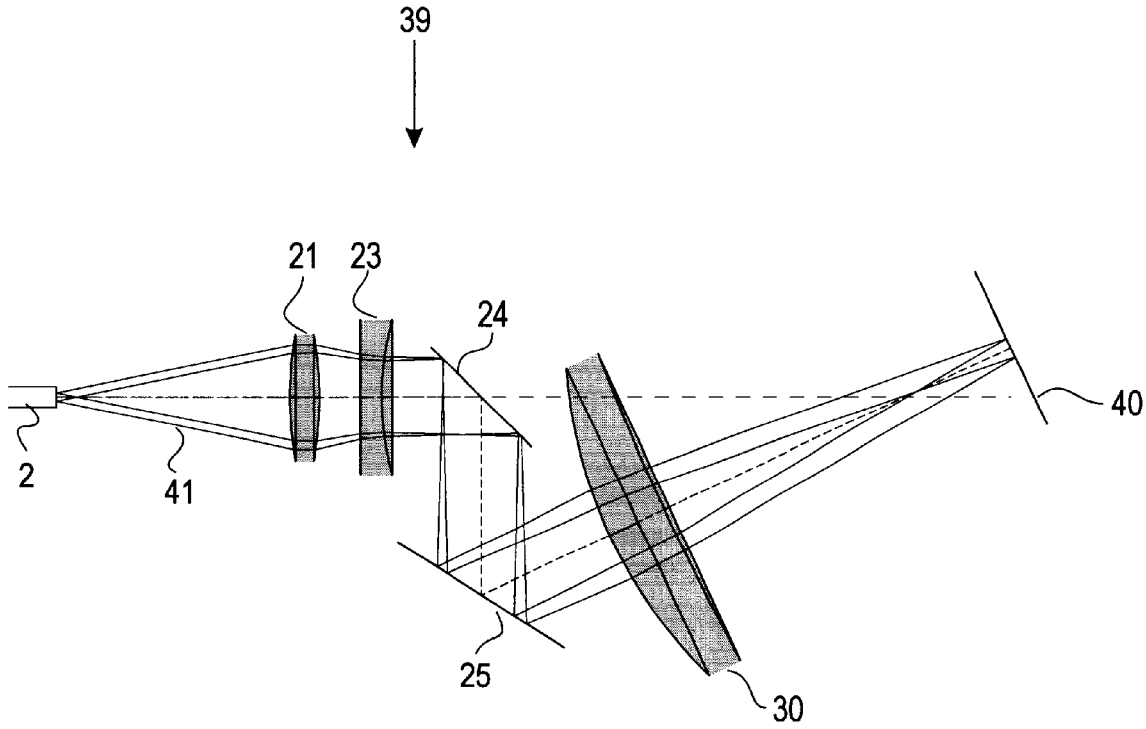
FIG. 3 shows the lens system of the handpiece shown in FIG. 2 in treatment mode in greater detail.

In FIG. 3, the lens system 39 is shown in greater detail. The light beams radiated from the outlet end of the fibers 2, 6, 7 are focused by the first focusing lens 21 and collimated by the collimating lens 23. The collimated light beam is transmitted from the collimating lens 23 via the deflecting means comprising a first mirror 24 and a second mirror 25 to a second focusing lens 30 which focuses the light beams on the target 40, which e.g. can be the facial tissue of a human being.

As shown in FIG. 2, the first mirror 24 is mounted on an indicator 45 of a galvanometer 26 positioned in the handpiece 38 of the tissue treatment apparatus according to the invention. When an electric current is sent through the coil of the galvanometer 26, the magnetic field generated by the current will make the indicator 45 rotate around the longitudinal axis of the indicator 45. The first mirror 24 will thereby by rotated, and the light beams will be deflected at an angle twice the angle rotated by the mirror 24.

The second mirror 25 is mounted on an arm 46 actuated by a linear actuator 29. When the linear actuator 29 activates the actuator arm 47, the arm 46, and thereby the second mirror 25, is rotated around the axle 48. A spring 28 is connected to one end of the arm 46 and to a non-moving part of the linear actuator 29 in the other end so as to neutralize wobble that may be present in the axle 48. When the second mirror 25 is rotated around the axle 48, the light incident on the second mirror 25 is deflected in an angle twice the angle rotated by the mirror 25. The linear actuator 29 may be controlled by applying a sequence of pulses across the terminals (not shown) of the actuator 29.

By controlling the current to the coil of the galvanometer 26 and the pulse sequence applied across the terminals of the linear actuator 29, the direction of light beams sent through the focusing lens 30 towards the target 40 can be controlled. It is thus possible to create different kinds of scan patterns of the light beam, such as rectangular or circular scan patterns.

A rotating arm 100 with a mirror 101 is by a solenoid 109 positioned in the beam path of the first laser light beam when the optical system is in a sensing mode as explained further below.

Figure 4:
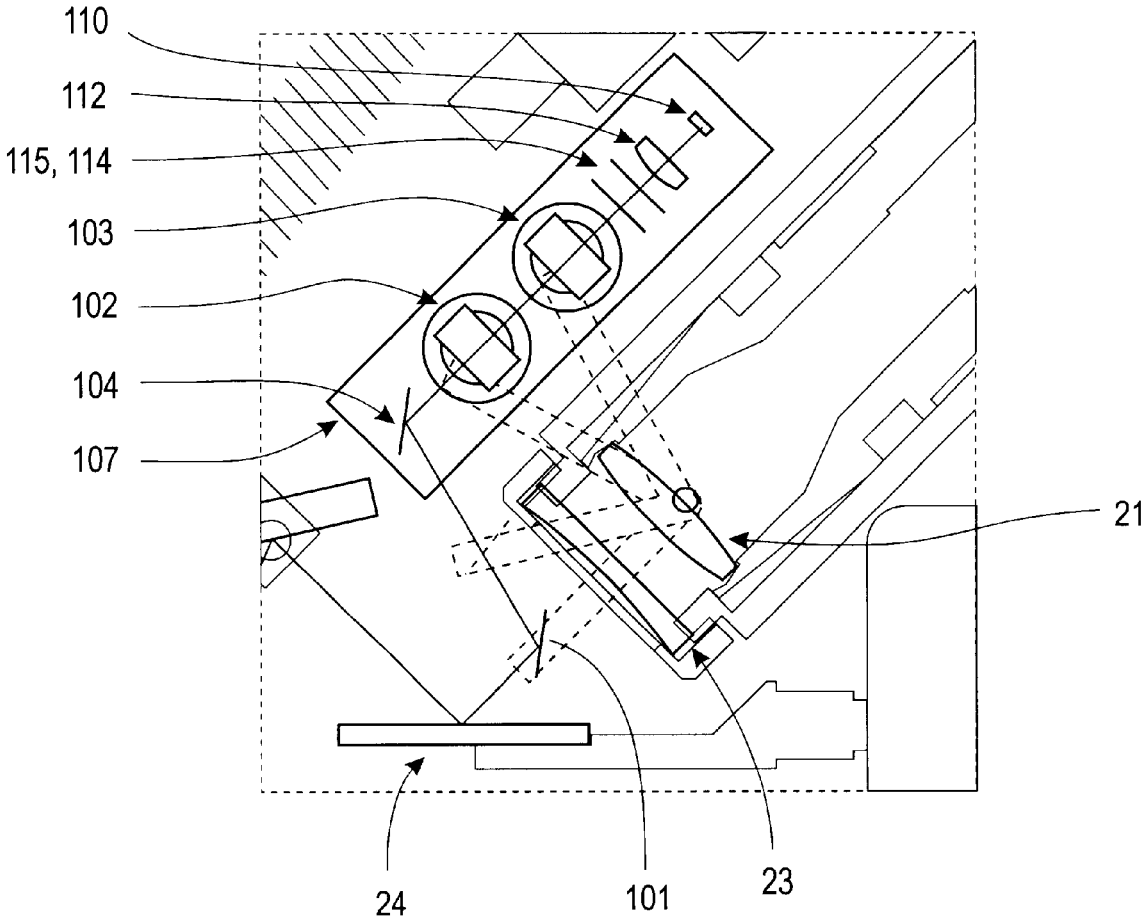
FIG. 4 shows the dashed area of FIG. 2, the detector means in more detail.

In FIG. 4, the part of the handpiece defined by the dashed line in FIG. 2 comprising the detector means is shown in greater detail. The detector means comprises a detector 110 and two light sources 102, 103 mounted in a holder for optical elements. The detector means further comprises a movable mirror 101. In sensing mode, the movable mirror 101 is positioned so as to transmit the sensing light beams emitted from the light sources 102, 103 mounted in the optical holder 107 via the fixed mirror 104 to the first mirror 24, the second mirror 25, and the second focusing lens 30 which focuses the light beams on the target 40. Likewise, the reflected sensing beams reflected from the target 40 are directed back to the detector means via the focusing lens 30 and the movable mirrors 24, 25. From the mirror 101 at the rotating arm 100 the reflected sensing beams are directed to the fixed mirror 104, wherefrom they are directed towards the detector 110 for intensity detection.

Figure 5:
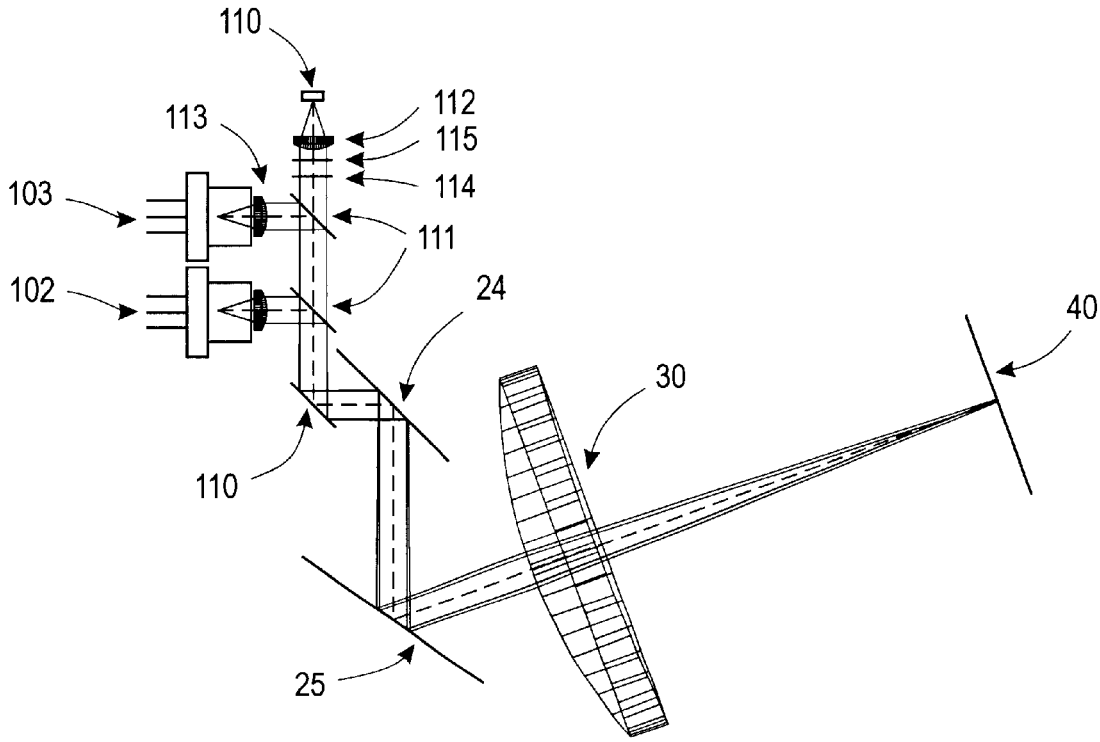
FIG. 5 shows detector means of the handpiece shown in FIG. 2 in sensing mode in greater detail.

In FIG. 5 the detector means are schematically shown in greater detail, where the fixed mirror 104, however, is omitted to facilitate understanding of the operation. The light sources 102, 103 are laser diodes which emit light at different wavelengths. The emitted sensing light beams are directed one at the time through collimating lenses 113 to collimate the beams and to beamsplitters 111 reflecting the sensing light beams towards the movable mirror 101 wherefrom the light is directed to the target 40 via mirror 24, mirror 25 and focusing lens 30. As the sensing light beams pass the same optical system as the light beams emitted from the outlet end of the fibers, they may be scanned across the target 40 and the position of the sensing beams will be known at any time. The beams reflected from the target 40 follow the same path back to the beamsplitters 111. The polarisation of the light beams is changed when the light is reflected from the target 40, and since the transmittance of the beamsplitters 111 are dependent on the polarisation of the incident light beam the reflected sensing light beams reflected from the target 40 are transmitted through the beamsplitters, without reflection. Before the beam reaches the detector 110, it passes a polarisation filter 114 and a blockout filter 115 to increase signal to noise ratio, and a third focusing lens 112 to focus the beam at the detector. To determine the type of tissue at the target 40 a red and a green light beam from respectively light sources 102, 103, respectively, are alternately directed towards the target 40. The reflection of the red and the green light beams, respectively, from the target 40 are directed to the detector by the deflection means and are detected at the detector 110. The differences in the reflected light from light sources 102, 103 are calculated and the type of tissue, i.e. the color of the tissue, to be treated is thereby determined. Depending upon the type of tissue parameters to be determined, it is of course envisaged that the sensing beams may be visible light beams of any color, or it may be ultra violet light beams, or it may be infrared light beams.

The optics and electronics of the handpiece 38 are protected by a plastic housing 36 provided in an ergonomical shape. An air tube 34 may be positioned on the handpiece 38 for providing suction of air from in front of the optics of the handpiece 38 in order to absorb any material ablated from the tissue of the object being treated with the apparatus of the present invention.

The light beams from the two glass fibers 6, 7 transmitted from the cable 1 through the optics of the handpiece and to the object, intersects at a distance equal to the focal length of the focusing lens 30, i.e. at the distance where the light from the $CO_2$ laser is focused. This is the distance at which the handpiece should be held from the object to get the best treatment result, and the intersection of the two visible light beams helps the operator keeping the correct distance to the tissue surface.

Because of the importance of keeping the $CO_2$ focal point on the tissue surface, the presently preferred embodiment of the handpiece 38 further comprises a magnetic distance member 33 connected to the handpiece 38 with a magnet 32. As the distance member 33 is magnetic, it is easy to connect to and disconnect from the handpiece 38.

In the apparatus here shown the detector detects the light and calculates the type of tissue to be treated, but it is also possible to include an infrared light detector for determination of the temperature of the target.

Furthermore, in the apparatus shown a mirror 101 is mounted on the rotating arm 100, whereby simultaneously sensing and treatment is not possible. By replacing the mirror with a beamsplitter, it is possible to simultaneously treat and sense.

The present handpiece has three functions each with 3 different modes. In the first function, the operator may choose between high, medium, or low scan speed modes. When scanning on different types of tissue, it is preferred to adjust the scan speed of the light beam in stead of adjusting the output power of the light beam. When scanning on tissue with a low absorption of light, such as dry skin, it is preferred to generate a high power density on the tissue, and the scan speed mode should be set to low. When scanning on tissue with an average absorption of light, the scan speed mode should be set to medium, and when scanning on tissue with a high absorbtion of light, the high scan speed mode should be selected.

In the second function, the operator may chose between three different modes defining three different scan patterns, which patterns are a line, a circular pattern and a quadratic pattern.

The third function enables the operator to choose between three different sizes of the scan pattern. If the scan pattern is quadratic, the area may be approx. 9*9 mm, approx. 6*6 mm, or approx. 3*3 mm, if the scan pattern is circular, the diameter of the circle may be approx. 9 mm, approx. 6 mm, or approx. 3 mm, and if the scan pattern is a line, the length of the line may be approx. 9 mm, approx. 6 mm, or approx. 3 mm.

Figure 6:
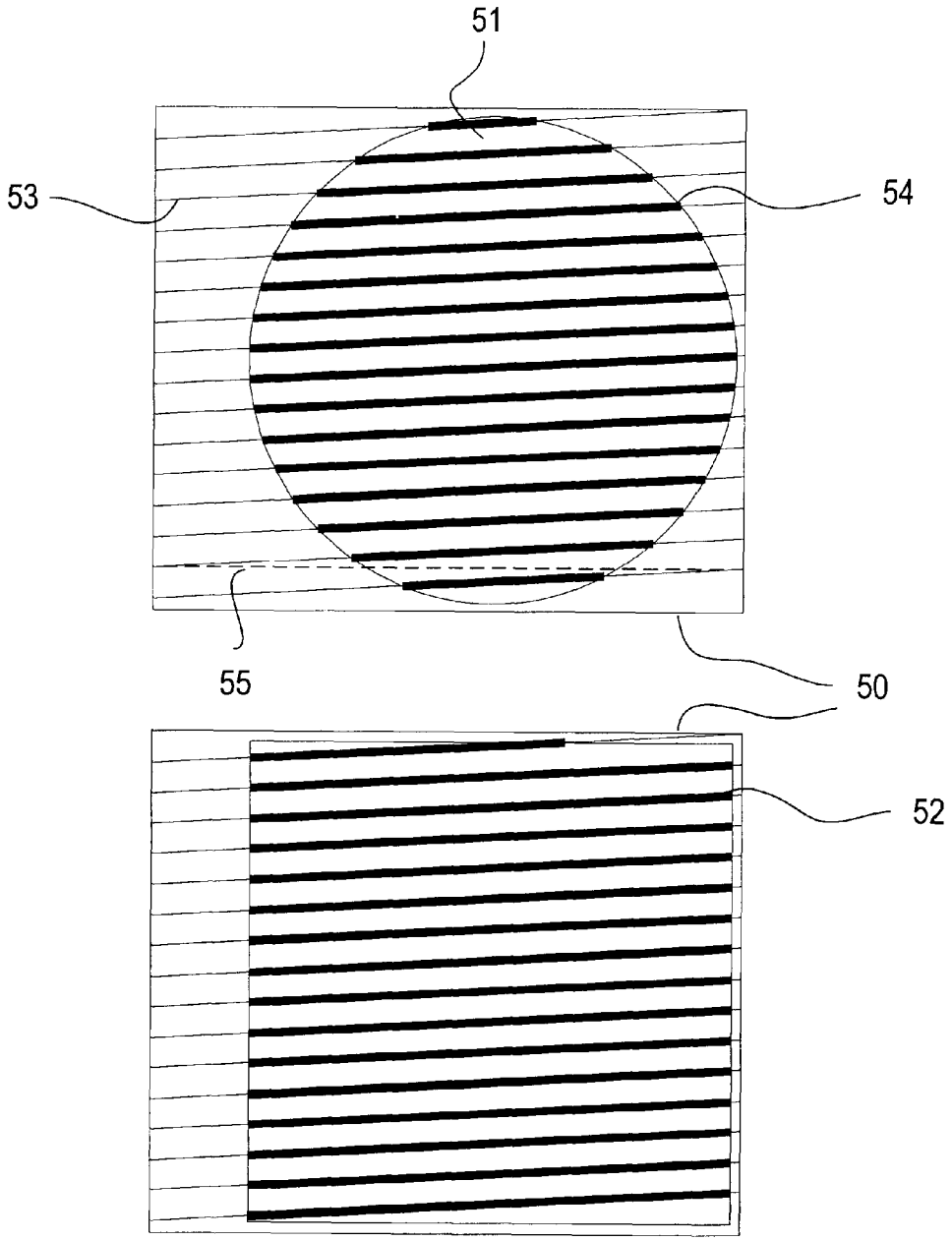
FIG. 6 shows a circular and a quadratic scan area.

In FIG. 6, a quadratic scan area 52 and a circular scan area 51 are shown. The actual laser scan area is indicated by reference numeral 50, but only the scan areas 51, 52 are used for tissue treatment. The thin lines 53 and the thick lines 54 indicate the path which the laser beam follows during a scan. The thin lines 53 indicate parts of the scan where the laser is turned off, while the thick lines 54 indicate parts of the scan where the laser is turned on.

The scan is performed as a slow forward/fast return-scan (a TV-scan, but without interlacing). The scan starts at the lower left corner of the actual scan area 50. The laser beam is moved towards the right, and when the laser beam enters the tissue treatment scan area 51 or 52, the laser is turned on. When the laser beam leaves the tissue treatment scan area 51 or 52, the laser is turned off, and when the laser beam reaches the right edge of the actual scan area 59, the beam is quickly retraced or moved to the left edge of the actual scan area 50, and a new scan line can be initiated.

In stead of turning the laser on and off, the speed of the movement of the laser beam may be increased to a speed sufficiently high for the laser beam not to ablate the tissue surface.

The fast movement (trace and retrace) of the laser beam between the right and left edges of the actual scan area 50, is accomplished by controlling the galvanometer 26. In order to let the mirror 24 settle after the fast movement from the right edge of the actual scan area 50 to the left edge, the first part of the scan line is not used for tissue treatment. The slower movement of the laser beam from the bottom to the top of the actual scan area 50 is accomplished by controlling the linear actuator 29 in a constant movement of the mirror 25.

A quadratic scan area of approx. 9*9 mm comprises 30 scan lines, and the max. scanning speed is app. 300 mm/s.

The operator of the apparatus controls the scanning using a pedal. When the pedal is activated, a scanning starts. After finishing the scanning, the $CO_2$ laser is turned off, and the visible light beam scans around at least a part of the circumference of the scan area 51 or 52 thereby indicating the size, shape and position of the scanned area 51 or 52. The operator may now move the handpiece and select a new scan area, e.g. a scan area abutting the area just scanned, and when the operator releases the pedal and again activates it, a new scanning will take place. In this way, the operator of the apparatus may easily scan larger areas of the tissue by scanning several neighbouring areas.

Figure 7:
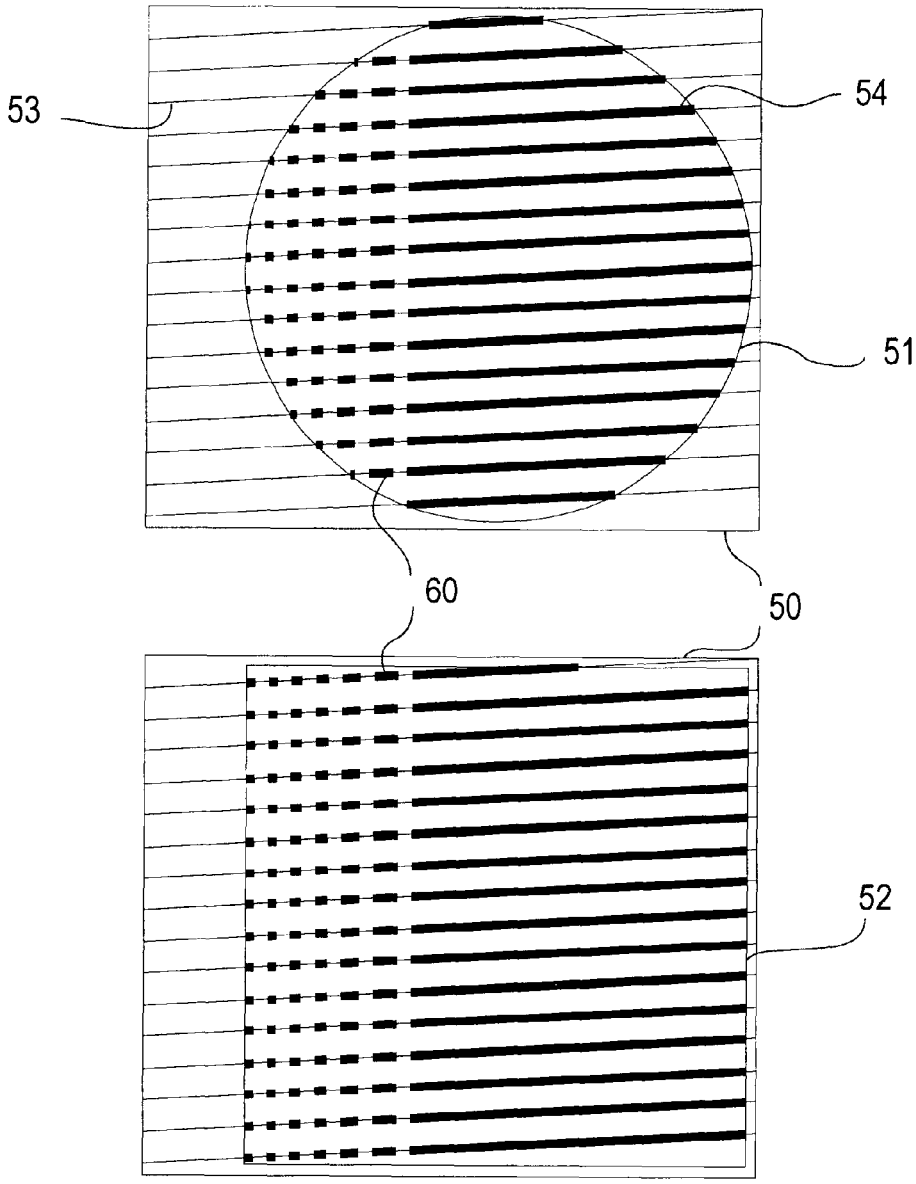
FIG. 7 shows a circular and a quadratic scan area with a single-sided fade-out scan pattern.

In FIG. 7, a quadratic scan area 52 and a circular scan area 51 with single-sided fade-out intensity scan lines 60 are shown. The fade-out intensity is accomplished by pulse modulating the laser power in shorter pulses as the intensity is faded out.

Figure 8:
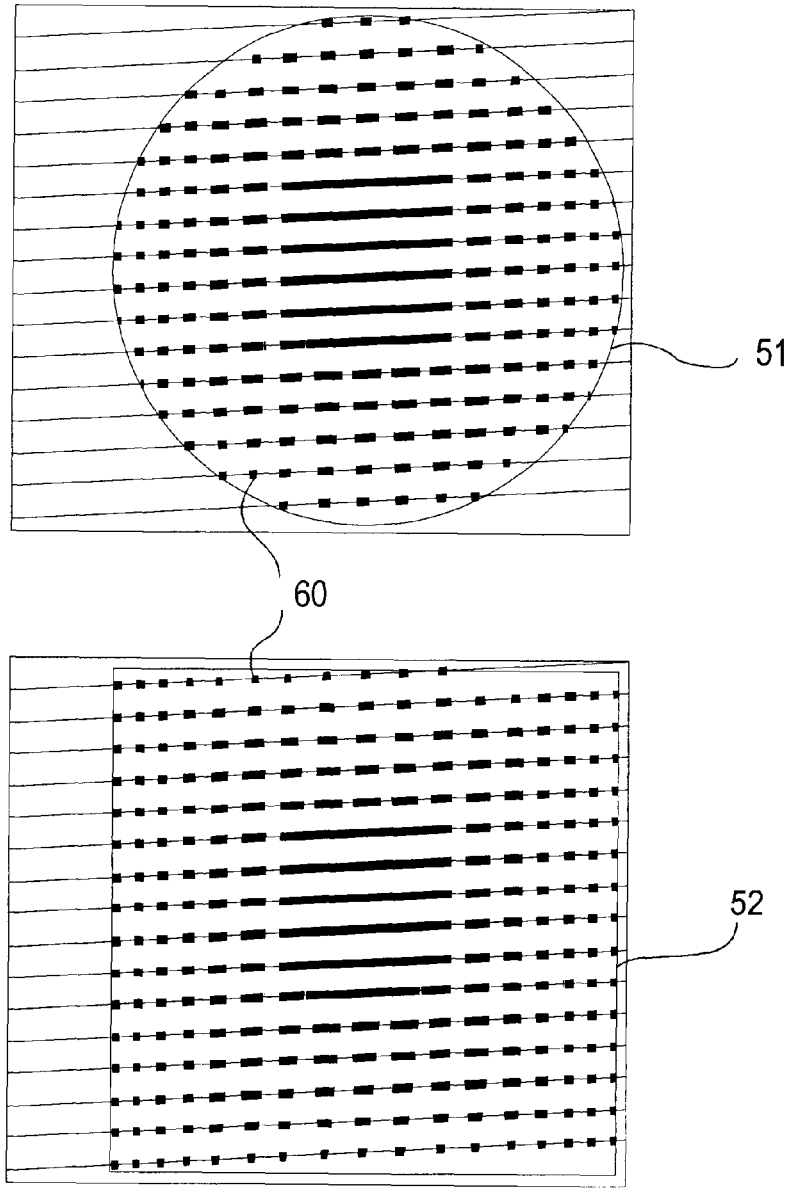
FIG. 8 shows a circular and a quadratic scan area with a four-sided fade-out scan pattern.

In FIG. 8, a quadratic scan area 52 and a circular scan area 51 with four-sided fade-out intensity scan lines 60 are shown.

The effect of using the fade-out intensity scan lines 60 is to create a smooth transition from a non-ablated area of the tissue to an ablated area.

The size and shape of the fade-in and fade-out scan areas may be selected using selectors on the handpiece 38.

It should be understood that a fade-in or a fade-out effect may be accomplished by gradually increasing or decreasing the intensity of the laser light, respectively, or by decreasing or increasing the speed of the movement of the laser beam, respectively.

In FIG. 9a, the beam profile for a standard laser beam transmitted via mirrors and standard lenses is shown. The beam profile is Gaussian with a high light intensity in the center of the beam. Only the high intensity center of the beam can ablate the tissue.

In FIG. 9b, a typical beam profile for a laser beam transmitted through the optical fiber 2 used in the apparatus according to the present invention is shown. The high intensity part of the beam profile is not limited to the center of the profile, but almost the complete beam profile has a sufficiently high intensity for ablating the tissue. When the laser light at 10.6 $\mu$m wavelength is transmitted through the 500 $\mu$m optical fiber 2, the laser light is changed from a single mode laser beam to a multi mode laser beam. A multi mode laser beam has a more uniform intensity profile compared to the single mode laser beam.

When using a Gaussian shaped beam, there is a risk of overexposing the tissue exposed by the center of the beam, while the parts of the tissue exposed by the edges of the beam are underexposed. This may result in thin lines of scars in the tissue. Using a non-gaussian shaped beam, as the beam provided by the optical fiber used in the apparatus according to the present invention, the risk of making scars in the tissue is minimized.

One of the advantages of using a broadened light beam is, that the risk of drawing lines on the tissue as with the high intensity Gaussian beam is minimized.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A handpiece for an apparatus for tissue treatment, comprising:

an input adapted to receive a first beam-outlet end *of* a first optical fiber for alignment of the first optical fiber with an axis of the handpiece so that a first light beam emitted from the first beam-outlet end is transmitted substantially along the axis;

first movable deflection means for variable deflection of the first light beam emitted from the beam-outlet end;

an output for emission of the deflected first light beam towards a target area of tissue to be treated;

first deflection control means for controlling the first movable deflection means in such a way that the first light beam is deflected along a predetermined path across the target area to be treated;

detector means for detecting the type of tissue a the target area; and first light beam control means for controlling parameters of the first light beam emitted towards the target area in response to the detected type of tissue whereby various types of tissue can automatically be treated differently.

2. The handpiece according to claim 1, wherein the detector means comprises light detectors for detection of intensity of light emitted from tissue at the target area.

3. The handpiece according to claim 1, wherein the detector means comprises infrared detectors for detection of temperature of tissue at the target area.

4. The handpiece according to claim 1, wherein the detector means comprises a detector array for detection of an image formed on the array.

5. The handpiece according to claim 4, further comprising image processing means for processing the image detected by the detector array.

6. The handpiece according to claim 5, wherein a size of a spot of light illuminated by the first light beam is calculatable by the imaging means.

7. The handpiece according to claim 6, further comprising:

output optics for focusing the first light beam onto the surface of tissue to be treated and movably positioned at the output of the handpiece; and focus control means for adjusting the position of the output optics in response to the value of the calculated spot size.

8. The handpiece according to claim 1, wherein the first movable deflection means comprises a first mirror that is rotatable around a first axis.

9. The handpiece according to claim 8, wherein the first movable deflection means further comprises a second mirror that is rotatable around a second axis.

10. The handpiece according to claim 9, wherein the first axis is substantially perpendicular to the second axis.

11. The handpiece according to claim 10, wherein the first movable deflection means is controllable by the first deflection control means to deflect the first light beam to scan the target surface area line by line.

12. The handpiece according to claim 1, further comprising tissue type storage means for storage of coherent data sets of signal values provided by the detector means at predetermined positions along the predetermined path of the first light beam and the corresponding positions of the deflecting means thereby mapping tissue parameters as a function of relative positions along the path in the storage means.

13. The handpiece according to claim 12, wherein the first light beam control means is adapted to control parameters of the first light beam during a second scan of the light beam along the predetermined path in accordance with the coherent data sets stored in the tissue type storage means.

14. The handpiece according to claim 1, further comprising a first probing light source for illuminating tissue at the target area and wherein light that is reflected from the illuminated tissue is detectable by the detector means.

15. The handpiece according to claim 14, further comprising a second probing light source for illuminating tissue at the target area and wherein the first and second probing light sources emit light of different wavelengths.

16. The handpiece according to claim 15, wherein each of the first and second probing light sources comprises a light emitting diode.

17. The handpiece according to claim 16, wherein the first probing light source comprises a light emitting diode for emission of light in a red wavelength range.

18. The handpiece according to claim 16, wherein the second probing light source comprises a light emitting diode for emission of light in a green wavelength range.

19. The handpiece according to claim 14, wherein the type of tissue is characterized by intensity of the light that is reflected from the illuminated tissue.

20. The handpiece according to claim 1, further comprising user interface means for selection of parameters of the handpiece.

21. The handpiece according to claim 20, wherein the parameters comprise a scan velocity.

22. The handpiece according to claim 20, wherein the parameters comprise a first light beam intensity.

23. The handpiece according to claim 20, wherein the parameters comprise a size of the target surface area.

24. The handpiece according to claim 20, wherein the parameters comprise a shape of the target surface area.

25. The handpiece according to claim 1, wherein the input is further adapted to receive a second beam-outlet end of a second optical fiber for transmission of a visible second light beam to the handpiece and for alignment of the second optical fiber with the axis of the handpiece so that the visible second light beam emitted from the second beam-outlet end is transmitted substantially in parallel with the axis, and further comprising second movable deflection means for variable deflection of the visible second light beam in such a way that the first and the second light beams emitted from the output of the handpiece illuminate substantially the same area of a target surface.

26. The handpiece according to claim 25, wherein the first and the second movable deflection means are identical.

27. The handpiece according to claim 25, further comprising second deflection control means for controlling the second movable deflection means and for controlling the second movable deflection means in such a way that the visible second light beam is scanned around at least a part of a circumference of the target surface area thereby indicating the size, shape and position of the target surface area.

28. The handpiece according to claim 27, wherein the shape of the target surface area is polygonal and the second deflection control means is further adapted to control the second moving means in such a way that the visible second light beam is scanned along one edge of the polygon.

29. The handpiece according to claim 1, further comprising a distance member connected to the handpiece at the output with fastening means and for indicating the desired distance between a patient and the output.

30. The handpiece according to claim 29, wherein the fastening means comprises a magnet so that the distance member can readily be disconnected from the handpiece.

31. The handpiece according to claim 1, wherein the first light control means executes either a fade-in or fade-out scan pattern in response to the tissue type determined by the detector means.

32. The handpiece according to claim 31, wherein the fade-in and fade-out scan patterns are effected by varying the intensity of the first light beam.

33. The handpiece according to claim 1, wherein the deflection control means executes either a fade-in or fade-out scan pattern in response to the tissue type determined by the detector means.

34. The handpiece according to claim 33, wherein the fade-in and fade-out scan patterns are effected by varying the scan speed of the first light beam.

* * * * *